United States Patent [19]
Dryden et al.

[11] Patent Number: 5,927,312
[45] Date of Patent: Jul. 27, 1999

[54] METHOD AND APPARATUS FOR EXTINGUISHING COMBUSTION WITHIN COMBUSTIBLE TUBING

[76] Inventors: Paul E. Dryden, 6329 W. Waterview Ct., McCordsville, Ind. 46055; Jeff Quinn, 512 Dorset Blvd., Carmel, Ind. 46268

[21] Appl. No.: 09/032,552

[22] Filed: Feb. 27, 1998

[51] Int. Cl.⁶ ................................................... F16K 17/38
[52] U.S. Cl. .................................. 137/1; 137/74; 137/75; 251/4
[58] Field of Search ................................. 137/1, 72, 74, 137/75; 251/4, 5, 11

[56] References Cited

U.S. PATENT DOCUMENTS

| | | | |
|---|---|---|---|
| 3,677,515 | 7/1972 | Fassler | 137/72 X |
| 3,720,153 | 3/1973 | Jardinier et al. | 137/75 X |
| 3,726,050 | 4/1973 | Wise et al. | 137/72 X |
| 4,136,707 | 1/1979 | Gaillot et al. | 137/75 |
| 4,143,670 | 3/1979 | Olson et al. | 137/72 |
| 4,143,671 | 3/1979 | Olson et al. | 137/72 |
| 4,404,983 | 9/1983 | Scheurenbrand et al. | 137/74 |
| 4,495,866 | 1/1985 | Brede et al. | 102/202 |
| 4,613,112 | 9/1986 | Phlipot et al. | 251/149.6 |
| 4,660,473 | 4/1987 | Bender et al. | 102/223 |
| 4,809,610 | 3/1989 | Florin | 102/205 |
| 4,843,965 | 7/1989 | Merzals | 102/205 |
| 4,884,595 | 12/1989 | Grove | 137/72 X |
| 5,392,825 | 2/1995 | Mims et al. | 137/614.2 |
| 5,398,714 | 3/1995 | Price | 137/102 |
| 5,676,712 | 10/1997 | Anderson | 48/192 |

*Primary Examiner*—John Rivell
*Attorney, Agent, or Firm*—Swanson & Bratschun LLC

[57] ABSTRACT

A self-extinguishing conduit for conveying a gas capable of supporting combustion of the conduit interior from an upstream to a downstream location includes a combustible tubing and a flow occluder operatively associated with the combustible tubing. The flow occluder is actuated by the heat of combustion within the combustible tubing to substantially halt the flow of gas through the combustible tubing. A combustion resistant material defines a select length of the conduit interior and is provided in series with the combustible tubing. The flow occluder is located downstream and proximate the combustion resistant material. A method for extinguishing combustion within a combustible conduit carrying a combustion supporting gas includes halting migration of combustion within the conduit at a select location and occluding the conduit at the select location.

29 Claims, 4 Drawing Sheets

METHOD AND APPARATUS FOR EXTINGUISHING COMBUSTION WITHIN COMBUSTIBLE TUBING

BACKGROUND OF THE INVENTION

1. Technical Field

The present invention is directed toward a safety device for oxygen delivery tubing, and more particularly toward a method and apparatus for extinguishing combustion within combustible tubing.

2. Background Art

It is a standard therapy for patients suffering from acute respiratory disorders to provide supplemental oxygen. A conventional oxygen delivery assembly includes a patient interface such as a nasal cannula, face mask, endotracheal fitting or the like with the supplemental oxygen being delivered to these patient interfaces from an oxygen supply by flexible plastic tubing, such as a polyvinyl chloride (PVC) tubing. In some instances, the oxygen delivery tubing is only several feet long and the oxygen supply is ambulatory. In other instances, the oxygen supply is stationary and the tubing is on the order of 50–100 feet long to enable the patient to move around a defined area while receiving supplemental oxygen.

Standard PVC oxygen tubing cannot sustain combustion under typical ambient conditions (i.e., oxygen concentration of 22%). However, if ignited in the presence of enriched oxygen (greater than 22%) the PVC tubing will burn aggressively. The PVC tubing can be ignited from exposure to an electrical short, cooking element, open flames such as candles and the like. However, it is believed that the most common cause of ignition of oxygen delivery PVC tubing is exposure to flames and sparks associated with smoking. Once the PVC tubing is ignited, the flame initially starts as an external fire and then moves to the tubing interior and migrates rapidly upstream toward the oxygen source. Should the migration of the combustion be arrested by encountering a non-combustible fitting, such as a metal connector, combustion will intensify within the PVC tubing adjacent the connector, eventually burning through the PVC tubing and causing a radical external flame which presents a severe risk of spreading the fire beyond the tubing. Under standard flow rates of 2–6 liter per minute and pressures of 4–7 psi, the point of combustion migrates at approximately one foot per second within the tubing. The precise rate of migration of the flame is dependent on the rate of oxygen flow, with the point of combustion migrating more quickly as the rate of oxygen flow increases.

The fire hazard of standard oxygen delivery assemblies in clinical settings is significant, but is typically mitigated by supervision of the patients, mandatory smoke detectors, fire alarms and other institutional safety practices such as strictly enforced no smoking policies. However, in jurisdictions not having these safety controls, the potential for catastrophic fires is considerably enhanced.

In the last several years, in an effort to control spiraling healthcare costs, considerable efforts have been dedicated to treating patients outside of clinical settings such as the patient's homes. Typically these alternative care locations do not include the many safeguards of the clinical setting. In addition, private homes can present an abundance of hazards such as substandard electrical appliances and cooking facilities that are not generally present in the clinical setting. Moreover, outside of the clinical setting there are fewer restrictions on the patient's behavior. It is much easier for the patient to engage in potentially hazardous activities, such as smoking. Thus, in these settings the potential for catastrophic fires is enhanced. Unfortunately, the prior art has done little to minimizes the serious fire risk at the source. Thus, patients, who are often ill-equipped to do so, are left to combat a fire after it has spread from the oxygen delivery assembly.

Mims et al., U.S. Pat. No. 5,392,825, is directed to a pressure regulator with an integral flashback arrester. The flashback arrester consists of a check valve and a porous metal flashback arrester manufactured from powered stainless steel sintered to form an elongate cup-like structure. In normal operation, combustible gas from a pressurized gas source flows in a downstream direction through the check valve. The flow of the gas unseats a disk within the check valve. In the event of a flashback, increased pressure will occur upstream of the check valve, thus biasing the disk to a seated position, thereby preventing flow of the flashback into the regulator and temporarily interrupting flow of the combustible gas. Mims further teaches that should the flashback pass through the check valve, the porous metal flashback arrester should extinguish the flashback.

The structure of Mims is complicated and, therefore, relatively expensive which would inhibit its widespread use as part of an oxygen delivery assembly. In addition, Mims does not intend to permanently halt the flow of combustible gas once a flashback occurs. Rather, once the flashback is arrested, flow of the combustible gas would begin again which could create a renewed hazard.

Anderson, U.S. Pat. No. 5,676,712, is also directed to a flashback protection apparatus. Anderson describes an apparatus for stopping a flashback of flame in a combustible gas conduit by using a "bolus" or bulk volume of non-combustible gas introduced into the conduit to halt the progress of the flashback. Anderson suffers the same shortfall of Mims in that it is a complicated, expensive structure. Furthermore, Anderson does not provide for permanently cutting off the flow of combustible gas.

The present invention is directed toward overcoming one or more of the problems discussed above.

SUMMARY OF THE INVENTION

A first aspect of the present invention is a self-extinguishing conduit for conveying a gas capable of supporting combustion of the conduit interior from an upstream to a downstream location. The self-extinguishing conduit consists of a combustible tubing and a flow occluder operatively associated with the combustible tubing, the flow occluder being actuated by the heat of combustion within the combustible tubing to substantially halt the flow of gas through the combustible tubing. A combustion resistant material defining a first select length of the conduit interior can be provided in series with the combustible tubing. The first select length is sufficient to halt upstream migration of combustion of the tubing across the combustion resistant material. Preferably, the flow occluder is located downstream and proximate to the combustion resistant material. The flow occluder is preferably a heat contracting material formed in a band around a select length of the combustible tubing exterior, the heat contracting material contracting upon being heated above a select temperature to pinch the tubing and thereby, halt the flow of gas. In another preferred embodiment, the flow occluder is a heat expanding material disposed within the tubing interior. The heat expanding material expands upon being heated above a select temperature to occlude the tubing interior and thereby substantially halt the flow of gas through the combustible tubing. The combustion resistant material may be in the form of an adapter for joining ends of the combustible tubing lengths into a continuous conduit. Alternatively, the combustion resistant material may be in the form of a lining to the tubing interior.

A second aspect of the present invention is an assembly for delivering oxygen from an upstream pressurized oxygen supply to a downstream location. The assembly includes an upstream length of tubing made of a combustible material defining a first conduit segment and a downstream length of tubing made of a combustible material defining a second conduit segment. An adapter made of a combustion resistant material defining a connecting conduit segment joins an end of the upstream length of tubing to an end of the downstream length of tubing with the connecting conduit segment joining the first and second conduit segments into a continuous conduit. A flow occluder is operatively associated with the downstream length of tubing proximate the adapter. The flow occluder is actuated by the heat of combustion of the combustible material within the combustible tubing to substantially prevent the flow of gas through the conduit. Preferably, the flow occluder is a band of heat contracting material around the downstream length of tubing having a first select inner diameter that does not substantially occlude the tubing and a second select diameter that substantially occludes the tubing, the band of heat contracting material being actuated between the first and second select diameters upon being heated above a select temperature. Alternatively, the flow occluder may, be a heat sensitive material lining an interior portion of the downstream length of tubing, the material expanding to substantially occlude the tubing upon being heated above a select temperature.

A third aspect of the present invention is an apparatus of extinguishing combustion within a closed conduit made of a combustible material conveying a gas capable of supporting combustion of the combustible material within the conduit interior from an upstream to a downstream location. The apparatus includes an arrester for halting upstream migration of the combustion within the closed conduit, the arrester being connectable between adjacent lengths of the closed conduit to define a portion of the conduit interior. An occluder is operatively associated with the arrester and is responsive to heat generated by the halted migration of combustion for substantially preventing the flow of gas through the conduit interior. The arrester is preferably an adapter adapted for joining the ends of adjacent conduit lengths into a continuous conduit, the adapter being made of a combustion resistant material. The occluder is preferably a heat contracting material that contracts upon being heated above a select temperature, the heat contracting material forming a band around the select length of the conduit exterior. The apparatus may further include a length of plastic tubing connectable to adjacent lengths of the closed conduit to define a portion of the closed conduit interior. The arrester comprises a lining to a portion of the plastic tubing interior and the occluder is operatively associated with the length of plastic tubing to occlude the interior of the length of plastic tubing upon being heated above a select temperature.

Yet another aspect of the present invention is a method for extinguishing combustion within a closed conduit flowing a gas capable of supporting combustion within the conduit from an upstream supply to a downstream point of delivery. The method includes halting the migration of a point combustion toward the gas supply at a select location between the supply and a point of delivery and halting of the flow of gas at about the select location. Preferably, the halting of the flow of gas is accomplished by actuating a heat sensitive material at about the halted point of combustion by the heat of combustion to occlude the conduit interior.

The method and apparatus for extinguishing combustion within oxygen tubing of the present invention quickly and reliably extinguishes the combustion before igniting a fire external of the tubing. The apparatus is highly reliable and easily incorporated into standard oxygen delivery assemblies. Moreover, the apparatus is simple and inexpensive to manufacture and install, eliminating these otherwise serious impediments to widespread use.

DETAILED DESCRIPTION OF THE PREFERRED EMBODIMENT

Figure 1:
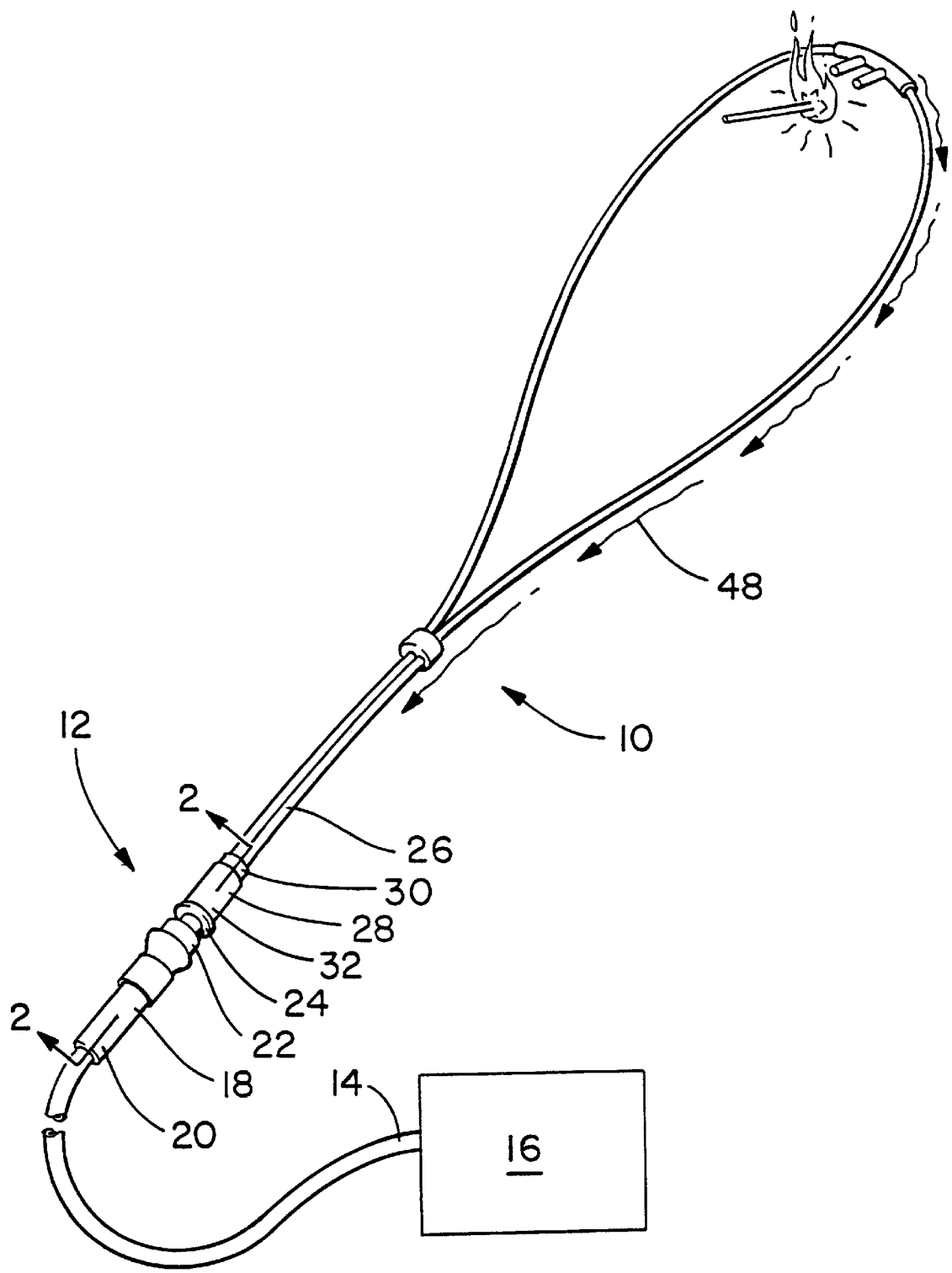
FIG. 1 is perspective view of an oxygen delivery assembly including the apparatus for extinguishing combustion within combustible tubing of the present invention.

An oxygen delivery assembly 10 including the apparatus for extinguishing combustion within oxygen tubing 12 of the present invention as illustrated in FIG. 1. With the exception of the apparatus 12, the assembly 10 is conventional and well known in the art. The oxygen delivery assembly consists of a first length of a combustible tubing, for example polyvinyl chloride (PVC) tubing, which extends from an oxygen supply 16 at a first end to a connector 18 at a second end. The connector 18 receives at a first end 20 the second end of the tubing which is typically solvent or heat bonded therein. The second end 22 of the connector 18 is configured to receive one end of a double male adapter 24. In a conventional assembly, the double male adapter 24 is made of a combustible plastic. A second length of combustible tubing 26 has a first end received within a first end 30 of connector 28 in the same manner discussed above with regard to connector 18. The connectors 18 and 28 are also made of combustible materials and one or both may be swivel connectors. The second end 32 of the connector 28 in turn receives a second end of the double male adapter 24 to create a continuous conduit consisting of the first length of combustible tubing 14 (including the connector 18), the second length of combustible tubing 26 (including the connector 28) and the adapter 24. The connectors 18, 28 and the adapter 24 are collectively referred to as a collector assembly herein. As illustrated in FIG. 1, the second length of tubing 26 is divided into two channels which deliver oxygen to a nasal cannula 34 for administering oxygen to a patient. While the particular embodiment illustrated in FIG. 1 shows a nasal cannula 34, other patient interfaces may be substituted for delivering oxygen to the patient, depending upon the patients requirements, such as a face mask, an endotracheal tube connection or the like. Indeed, simply delivering the oxygen to a tent enveloping the patient would also be a suitable patient interface.

The oxygen supply 16 is intended to include air, mixtures of gases with an oxygen concentration greater than that of air, and pure oxygen. In a broad sense, the oxygen supply may be any gas capable of supporting combustion of the combustible tubing, which necessarily means it includes some measure of oxygen.

Figure 2:
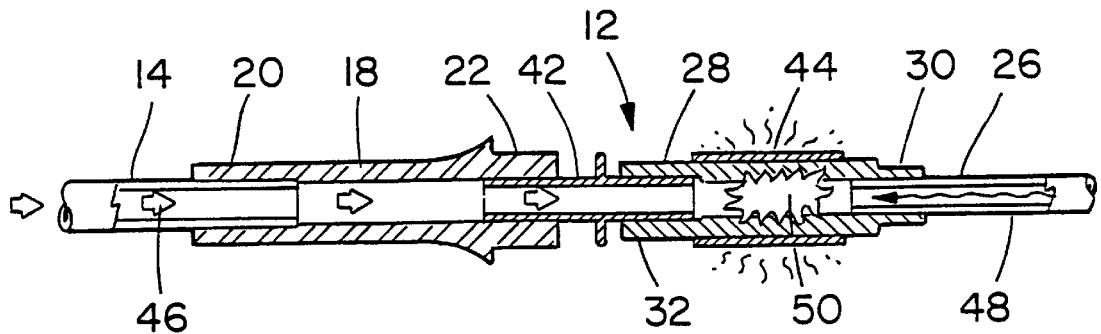
FIG. 2 is a cross-section of the apparatus for extinguishing combustion within combustible tubing taken along line 2—2 of FIG. 1.

FIG. 2 is a first embodiment of the apparatus 12 for extinguishing combustion within the oxygen tubing of the present invention incorporated in a connector assembly. Referring to FIG. 2, the first length of combustible tubing 14 is shown inserted within the first end 20 of the standard connector 18. Here, the double male adapter 42 is made of combustion resistant material such as metal or heat resistant plastic. As used herein, combustion resistant means a material which will not ignite in the presence of combustion supporting gas (e.g., oxygen) conveyed by the tubing, or at least will not ignite for a period sufficient for heat sensitive material 44 to occlude the conduit. One end of the adapter 42 is received within the second end 22 of the connector 18 and the other end of the adapter 42 is received within the second end 32 of the second connector 28. The second connector 28 has a heat sensitive material 44 formed as a band around the outer diameter of the connector 28. Finally, the second length of tubing 26 is received within the first end 30 of the connector 28 to form a continuous conduit for supplying oxygen from an upstream to a downstream location as indicated by the arrows 46.

Figure 3:
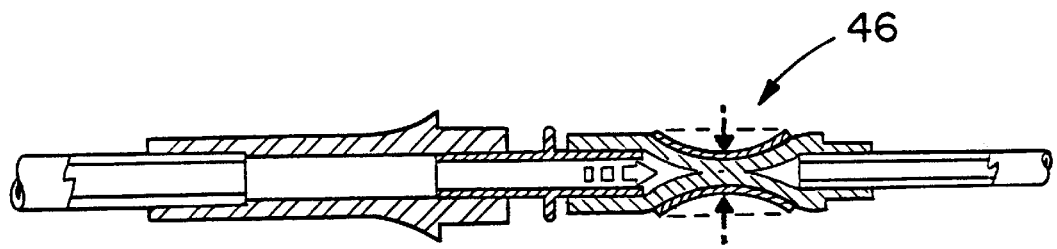
FIG. 3 is a cross-section of the apparatus of FIG. 2 illustrating the conduit occluded.

The heat sensitive material 44 has a first select inner diameter that does not substantially occlude the connector 28 and a second select diameter that substantially closes or occludes the connector 28. This second select diameter is illustrated at 46 in FIG. 3. The heat sensitive, or more particularly, heat contracting material, is actuated between the first select diameter and the second select diameter upon being heated above a select temperature. The precise temperature is material specific. A material which is actuated at a low temperature (e.g. 70° C.) is preferred, but the temperature must not be so low as to inadvertently actuate during normal transport and handling.

In operation, internal combustion within the second length of combustible tubing 26 migrates from a downstream to an upstream direction toward the oxygen source as illustrated by the arrows 48 of FIGS. 1 and 2. As the flame moves into the extinguishing apparatus or connector assembly 12 it encounters the double male adapter 42 made of combustion resistant material which halts further migration of the point of combustion 50 in the upstream direction. The double male adapter is long enough to prevent the combustion from spanning it. A length of 0.75–1.5 inches has been found suitable for oxygen pressures of up to 10 psi and flow rates of 10 liters per minute. With the point of combustion 50 prevented from further migration, the continued supply of oxygen maintains the point of combustion 50 immediately downstream from the combustion resistant adapter 42 and causes heat to build up at that point. The build up of heat causes the wall of the connector to soften and become more pliable. As the point of combustion is sustained at this location, the heat sensitive material 44 is eventually heated to the select temperature which causes it to contract as illustrated at 46 of FIG. 3, thereby preventing further flow of oxygen to the point of combustion 50, which in turn extinguishes the internal combustion within the conduit. Alternatively, the connector 28 could be made of a heat sensitive material that contracts on itself to pinch off the conduit. Although not separately illustrated, this embodiment is readily understood by reference to FIGS. 1 and 2.

Figure 4:
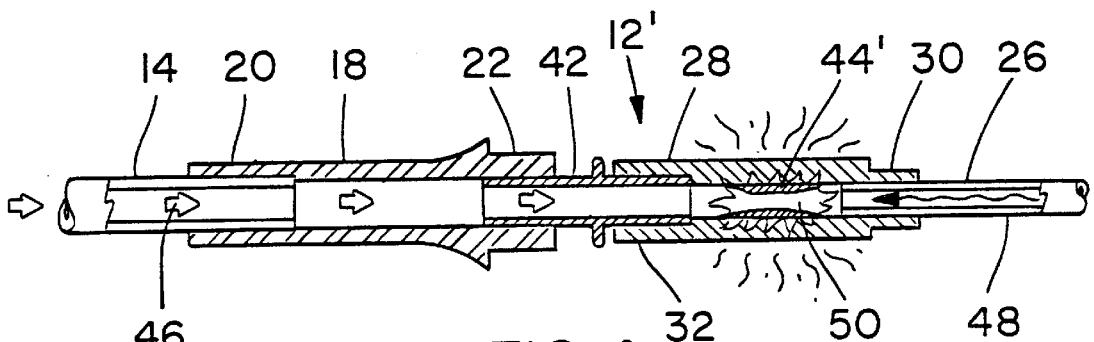
FIG. 4 is a cross-section of an alternate embodiment of the apparatus of FIG. 2 including a heat expansive material disposed within the conduit.
Figure 5:
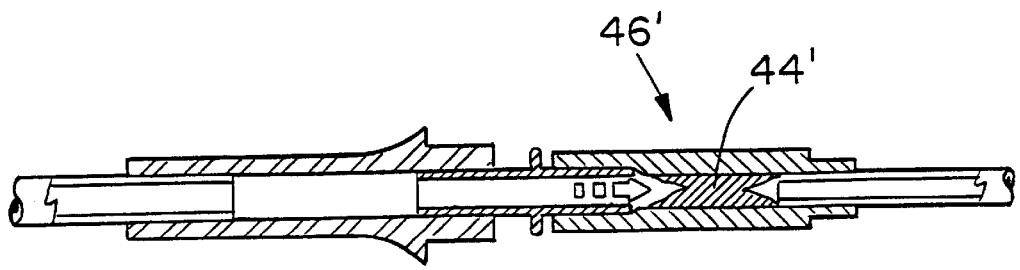
FIG. 5 is a cross-section of the apparatus of FIG. 4 illustrating the conduit occluded.

FIG. 4 illustrates a second embodiment of the apparatus incorporated into a connector assembly designated as 12'. This embodiment is identical to that depicted in FIG. 2 with like parts identified with like reference numerals, except for the heat sensitive material 44'. In this embodiment, the heat sensitive material 44' expands when subjected to the heat of combustion by the point of combustion 50 to occlude the conduit at 46' as illustrated in FIG. 5.

Figure 6:
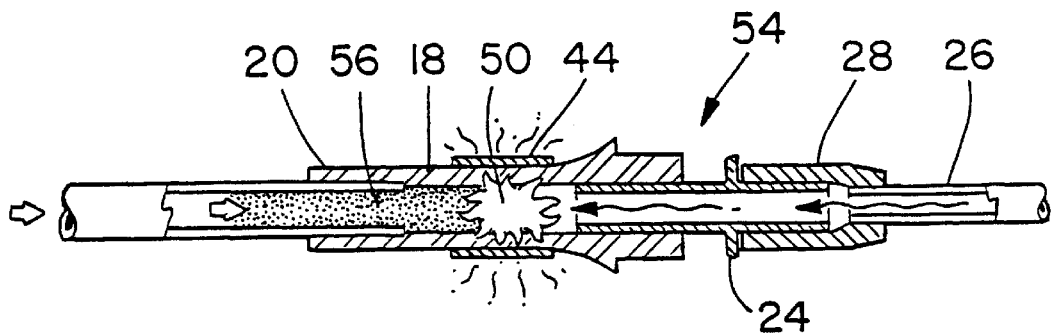
FIG. 6 is a cross-section of an alternate embodiment of the apparatus of FIG. 2, including a non-combustible lining in the connector adjacent the heat sensitive occluder.

FIG. 6 illustrates a third embodiment 54 of the apparatus for extinguishing combustion within oxygen tubing incorporated into a connector assembly. In this embodiment, the connector 28 at the end of the second length of combustible tubing 26 is conventional and the adapter of the double male adapter 24 is also conventional in that it is made of a combustible thermal plastic. The connector 18 is modified in that it includes a layer of combustion resistant material 56 proximate the first end 20. This layer of combustion resistant material could be a metal liner, embedded glass beads or the like, which are not combustible when exposed to the heat of combustion of the point of combustion 50. A heat sensitive material 44 is formed as a band around the connector immediately downstream of the combustion resistant material 56. Similar to the first embodiment discussed above with reference to FIG. 2, as the point of combustion 50 encounters the combustion resistant material 56 further migration of the point of combustion upstream toward the oxygen source is halted. Again, this layer is long enough to halt migration of the combustion. The heat of combustion generated by the point of combustion 50 serves to soften the connector wall at the point of combustion and further heats the heat sensitive material 44 which then contracts to its second contracted diameter, thereby halting further flow of oxygen through the conduit which, in turn, extinguishes the combustion 50. Alternatively, and as discussed above with regard to FIG. 4, the heat sensitive material 44' could be a heat expansive material which, when exposed to the heat of combustion, expands to occlude the lumen as illustrated at 46' of FIG. 5.

Figure 7:
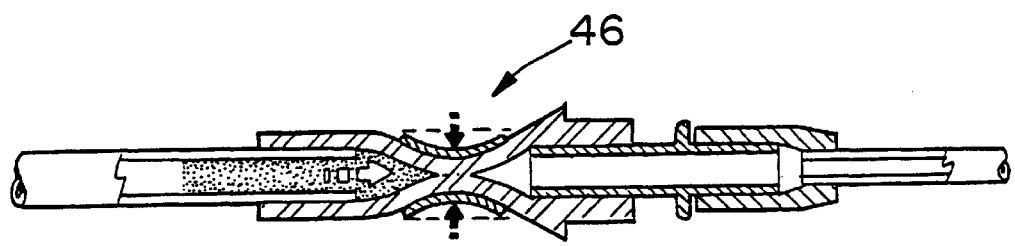
FIG. 7 is a cross-section of the apparatus of FIG. 6 illustrating the conduit occluded.
Figure 8:
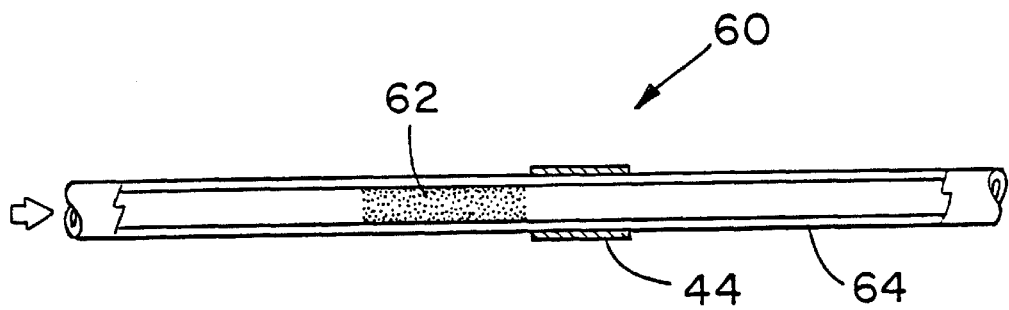
FIG. 8 is a cross-section of an alternate embodiment of the apparatus for extinguishing combustion within combustible tubing.

FIG. 8 is a fourth embodiment of the present invention. In FIG. 8 the apparatus 60 for extinguishing combustion within oxygen tubing consists of a combustion resistant material layer 62 disposed within a conventional combustible tubing 64 with a heat sensitive material 44 immediately upstream from the combustion resistant material layer 62. As illustrated and described above with regard to FIG. 6, as a point of combustion moves from downstream toward upstream and the oxygen supply, the point of combustion would be halted immediately upstream of the combustion resistant layer 62 thereby heating the heat sensitive material 44 to actuate it to assume its second diameter, thereby preventing the flow of gas and extinguishing the internal combustion. Of course, as described above with reference to FIGS. 6 and 7, the heat sensitive material 44 could also be a heat expansive material disposed within the tubing and would then function as discussed with regard to FIGS. 4 and 5.

Figure 9:
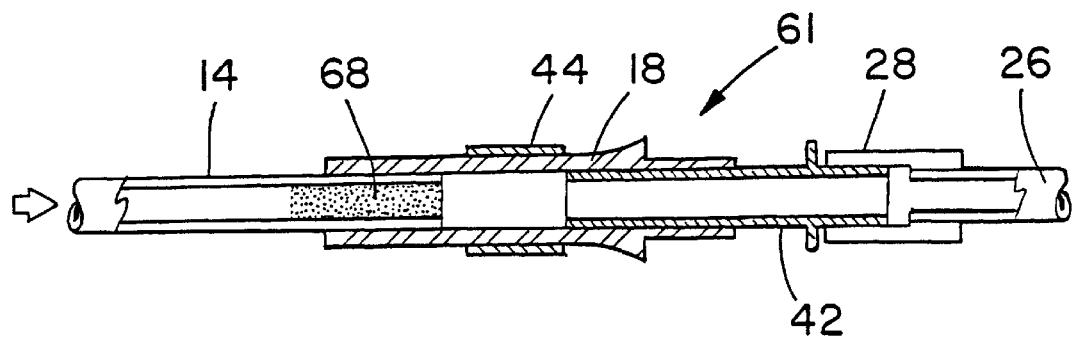
FIG. 9 is a cross-section of an alternate embodiment of the apparatus for extinguishing combustion within combustible tubing of FIG. 2.

FIG. 9 is a fifth embodiment 61 of the apparatus for extinguishing combustion within an oxygen tubing of the present invention incorporated into a connector assembly. In this embodiment, the connector 18, double male adapter 42, the connector 28 and the second length of combustible tubing 26 are all of conventional makeup. The first length of combustible tubing 14 includes a combustion resistant layer 68 of the nature of the combustion resistant layer 62 discussed above with reference to FIG. 8. Here the combustion resistant layer need only be at the end of the tube 14, facilitating its manufacture. A band of heat sensitive material 44 surrounds the connector 18 as illustrated and would function to close the conduit when subject to the heat of combustion as discussed above with reference to FIGS. 2–3, 6–7 and 8. Of course, the heat sensitive material 44 could be a heat expansive material 44' disposed within the connector 18 as discussed above with reference to FIGS. 4 and 5.

Figure 10:
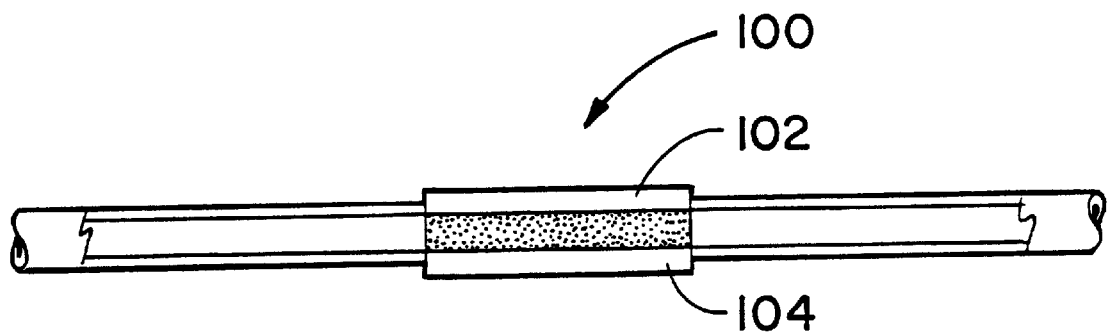
FIG. 10 is a cross-section of another alternate embodiment of the apparatus for extinguishing combustion within combustible tubing.

FIG. 10 is a sixth embodiment 100 of an apparatus for extinguishing combustion within a combustible tubing. In this embodiment an insert 100 is provided between adjacent lengths of combustible tubing. The insert 100 has a shell 102 made of a combustible material and an interior filling 104 of a sintered thermoplastic. The sintered thermoplastic forms tortuous paths for the combustion supporting gas flowing through the insert. When the flash back or point of combustion reaches the filling 104, the tortuous paths slows its progress and the heat of combustion melts the plastic forming the filling. The melting causes the tortuous to be blocked, thereby halting further flow of the gas and thereby extinguishing the combustion. It is believed this embodiment could halt flash backs of combustible gases as well as arresting migration of combustion within a combustible conduit carrying a combustion supporting gas.

For the ease of description, the apparatus for extinguishing combustion within oxygen tubing has been discussed as being embodied in a modified connector assembly. As would readily be appreciated by one skilled in the art, the apparatus for extinguishing combustion within the oxygen tubing could be modified to be located proximate the patient interface, such as the nasal cannula 34 illustrated in FIG. 1. Such an embodiment has the advantage of halting the point of combustion almost immediately at its most likely starting point, but has the disadvantage of adding weight and bulk proximate the patient interface.

The embodiments illustrated and described herein focus on an occluder which is made of a heat sensitive material that contracts or expands when heated to a select temperature. The invention could also contemplate a mechanical valve that is triggered by being heated above a select temperature, although such a heat actuated valve is not illustrated herein. Furthermore, the fundamental of the inventive concept, which includes arresting the migration of the point of combustion at a select point and using that heat of combustion at that point to actuate an occluder could be embodied in other combinations of elements than those illustrated herein that are still considered to be with the scope of the inventive disclosure.

The method and apparatus for extinguishing combustion within oxygen tubing of the present invention is inexpensive to assemble and deploy, which will vastly enhance the likelihood of this important safety feature getting widespread acceptance and use. The apparatus is self-actuating and elegant in its simplicity, which leads to a high degree of reliability. The method and apparatus are readily adapted to conventional combustible oxygen tubing and connector assemblies which will also encourage their use and minimize cost.

What is claimed is:

1. A self-extinguishing conduit for conveying a gas capable of supporting combustion of the conduit interior from an upstream to a downstream location, the conduit comprising:

combustible tubing; and a flow occluder operatively associated with the combustible tubing, the flow occluder being actuated by the heat of combustion within the combustible tubing to substantially halt the flow of gas through the combustible tubing.

2. The self-extinguishing conduit of claim 1 further comprising:

a combustion resistant material defining a first select length of the conduit interior operatively associated with the combustible tubing, the first select length being sufficient to halt upstream migration of combustion of the tubing across the combustion resistant material.

3. The self-extinguishing conduit of claim 2 wherein the flow occluder is located downstream and proximate the combustion resistant material.

4. The self-extinguishing conduit of claim 2 wherein the halting of the upstream migration by the combustion resistant material causes an increase in the temperature of the outer surface of the tubing during combustion of the tubing interior at a second select length of the tubing proximate and downstream from the combustion resistant material, the flow occluder being located along the second select length of tubing.

5. The self-extinguishing conduit of claim 2 wherein the flow occluder comprises a heat contracting material that contracts upon being heated above a select temperature, the heat contracting material forming a band around a select length of the tubing exterior.

6. The self-extinguishing conduit of claim 2 wherein the flow occluder comprises a heat expanding material that expands upon being heated above a select temperature, the heat expanding material being disposed within the tubing interior.

7. The self-extinguishing conduit of claim 1 further comprising an adapter joining ends of combustible tubing lengths into a continuous tubing, the adapter forming a segment of the continuous conduit, the adapter being made of a combustion resistant material.

8. The self-extinguishing conduit of claim 7 wherein the flow occluder is proximate at least one end of the tubing lengths joined by the adapter.

9. The self-extinguishing conduit of claim 2 wherein the combustion resistant material is a lining to the tubing interior.

10. The self-extinguishing conduit of claim 1 wherein the flow occluder comprises a length of plastic tubing attached to the combustible tubing that contracts to pinch off the interior of the plastic tubing when heated above a select temperature.

11. An assembly for delivering oxygen from an upstream pressurized oxygen supply to a downstream location, the assembly comprising:

an upstream length of tubing made of a combustible material defining a first conduit segment;

a downstream length of tubing made of a combustible material defining a second conduit segment;

an adapter made of a combustion resistant material defining a connecting conduit segment, the adapter joining an end of the upstream length of tubing to an end of the downstream length of tubing with the connecting conduit segment joining the first and second conduit segments into a continuous conduit; and a flow occluder operatively associated with the downstream length of tubing proximate the adapter, the flow occluder being actuated by the heat of combustion of the combustible material within the tubing to substantially prevent the flow of gas through the conduit.

12. The assembly of claim 11 wherein the adapter is made of one of metal and a combustion resistant plastic.

13. The assembly of claim 11 wherein the flow occluder comprises a band of heat contracting material around the downstream length of tubing having a first select inner diameter that does not substantially occlude the tubing and a second select diameter that substantially occludes the tubing, the band of heat contracting material being actuated between the first and second select diameters upon being heated above a select temperature.

14. The assembly of claim 11 wherein the flow occluder comprises a material lining a portion of the downstream length of tubing, the material expanding to substantially close the tubing upon being heated above a select temperature.

15. The assembly of claim 11 wherein the joined ends of the upstream and downstream segments of tubing each comprise a connector made of a combustible material mating at one end with an end of one of the segments of tubing and at the other end with the adapter, the flow occluder being operatively associated with the downstream connector.

16. An apparatus for extinguishing combustion within a closed conduit made of a combustible material conveying a gas capable of supporting combustion of the combustible material within the conduit interior from an upstream to a downstream location, the apparatus comprising:

halting means for halting upstream migration of combustion within a closed conduit, the halting means being connectable between adjacent lengths of a closed conduit to define a portion of the conduit interior; and occluding means operatively associated with the halting means, the occluding means being responsive to heat generated by the halted migration of combustion for substantially preventing the flow of gas through the conduit interior.

17. The apparatus of claim 16 wherein the halting means comprises an adapter adapted for joining the ends of adjacent conduit lengths into a continuous conduit, the adapter being made of combustion resistant material.

18. The apparatus of claim 16 wherein the halting means comprises a double male adapter made of one of metal and a combustion resistant plastic.

19. The apparatus of claim 16 wherein the occluding means comprises a heat contracting material that contracts upon being heated above a select temperature, the heat contracting material forming a band around a select length of the conduit exterior.

20. The apparatus of claim 16 wherein the occluding means comprises a heat expanding material that expands upon being heated above a select temperature, the heat expanding material being disposed in the conduit interior with the halting means connected between adjacent lengths of closed conduit.

21. The apparatus of claim 16 further comprising a length of plastic tubing, the length of plastic tubing being connectable to adjacent lengths of the closed conduit to define a portion of the conduit interior, the halting means comprising a lining to a portion of the plastic tubing interior and the occluding means being operatively associated with the length of plastic tubing to occlude the interior of the length of plastic tubing upon being heated above a select temperature.

22. The apparatus of claim 16 further comprising a length of plastic tubing having first and second ends, the length of plastic tubing being connectable at the first end to an end of a length of closed conduit, the halting means comprising an adapter made of a combustion resistant material having a first end connected to the second end of the length of plastic tubing and a second end adapted for connection to an end of closed conduit, the occluding means being operatively associated with the length of plastic tubing to occlude the interior of the length of plastic tubing upon being heated above a select temperature.

23. The apparatus of claim 22 wherein the occluding means is integrally formed of a single piece with a length of plastic tubing.

24. A method of extinguishing combustion within a closed conduit flowing a gas capable of supporting combustion with the conduit from an upstream supply to a downstream point of delivery, the method comprising:

a. halting migration of a point of combustion toward the gas supply at a select location between the point of supply and point of delivery; and b. halting the flow of the gas at about the select location.

25. The method of claim 24 wherein the gas is oxygen enriched and the closed conduit is made of a material capable of supporting combustion.

26. The method of claim 24 wherein step b. further comprises:

actuating a heat sensitive material at about the halted point of combustion by the heat of combustion to occlude the conduit interior.

27. The method of claim 26 wherein step b. further comprises:

occluding the conduit interior by pinching the conduit with the heat sensitive material.

28. The method of claim 27 wherein step b. further comprises:

softening the conduit by the heat of combustion.

29. The method of claim 26 wherein step b. further comprises:

providing a heat sensitive material that expands upon being heated above a select temperature within the conduit interior; and occluding the conduit interior by heating the heat sensitive material to above the select temperature by the heat of combustion.

* * * * *